United States Patent [19]
Floyd et al.

[11] Patent Number: 6,103,739
[45] Date of Patent: Aug. 15, 2000

[54] METALLOPROTEINASE INHIBITORS

[75] Inventors: Christopher David Floyd; Raymond Paul Beckett; Mark Whittaker; Andrew Miller, all of Oxford, United Kingdom

[73] Assignee: British Biotech Pharmaceuticals Limited, United Kingdom

[21] Appl. No.: 09/000,037

[22] PCT Filed: Jul. 22, 1996

[86] PCT No.: PCT/GB96/01737

§ 371 Date: Apr. 22, 1998

§ 102(e) Date: Apr. 22, 1998

[87] PCT Pub. No.: WO97/03783

PCT Pub. Date: Feb. 6, 1997

[30] Foreign Application Priority Data

Jul. 20, 1995 [GB] United Kingdom .................. 9514867

[51] Int. Cl.[7] .................. A61K 31/44; C07D 215/38; C07D 213/72; C07C 277/04; C07C 233/00
[52] U.S. Cl. .................. 514/313; 514/352; 514/371; 514/372; 514/620; 546/163; 546/309; 548/190; 548/214; 165/153
[58] Field of Search .................. 546/309, 163; 548/190, 214; 564/153; 514/313, 352, 371, 372, 620

[56] References Cited

FOREIGN PATENT DOCUMENTS

96/16027   5/1996   WIPO .

OTHER PUBLICATIONS

Hansen, J Nucl Med, 35 (7), pp. 1198–1205, 1994.
Hansen, Inorg Chem, 31(3), pp. 2801–2808, 1992.
CA 123:314549, Montana, 1995.

Primary Examiner—D. Margaret Seaman
Attorney, Agent, or Firm—Banner & Witcoff, Ltd.

[57] ABSTRACT

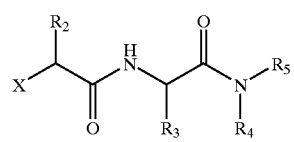

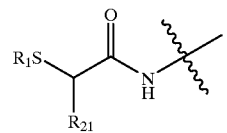

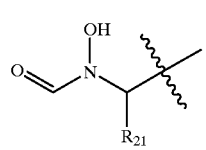

A compound of general formula (I), wherein X is a group of formula (II) or (III), $R_2$, $R_1$, $R_{21}$, $R_3$, $R_4$, and $R_5$ being as defined in the specification are matrix metalloproteinase inhibitors.

10 Claims, No Drawings

METALLOPROTEINASE INHIBITORS

The present invention relates to therapeutically active pseudopeptide or peptidyl compounds, to processes for their preparation, to pharmaceutical compositions containing them, and to the use of such compounds in medicine. In particular, the compounds are inhibitors of metalloproteinases involved in tissue degradation.

BACKGROUND TO THE INVENTION

The matrix metalloproteinases (MMPs) are a family of enzymes including interstitial collagenase, neutrophil collagenase, collagenase-3, 72 kDa gelatinase, 92 kDa gelatinase, stromelysin-1, stromelysin-2, stromelysin-3, matrilysin, macrophage metalloelastase, membrane-type metalloproteinase-1 and membrane-type metalloproteinase-2. These enzymes share a common zinc-containing catalytic domain and a pro-sequence which maintains latency. A wide range of cells and tissues can express MMPs in response to activation by inflammatory stimuli such as interleukin-1 or tumour necrosis factor a (TNF-α). Different stimuli can induce overlapping yet distinct repertoires of MMPs and different cell types can respond to the same stimuli by expression of distinct combinations of MMPs. MMPs can attack the protein components of extracellular matrix such as collagens, vitronectin and elastin, and have recently been shown to process membrane proteins such as pro-TNF-α to release soluble TNF-α. MMPs are thought to play a central role in the pathology of inflammatory diseases such as rheumatoid arthritis as well as in the growth and metastasis of tumours.

Compounds which have the property of inhibiting the action of MMPs are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas.

Many known MMP inhibitors are peptide derivatives, based on naturally occurring amino acids, and are analogues of the cleavage site in the collagen molecule. Chapman et al (J. Med. Chem. 1993, 36, 4293–4301) report some general structure/activity findings in a series of N-carboxyalkyl peptides. Other known MMP inhibitors are less peptidic in structure, and may more properly be viewed as pseudopeptides or peptide mimetics. Such compounds usually have a functional group capable of binding to the active site zinc (II) ion in the MMP, and known classes include those in which the zinc binding group is a hydroxamic acid, carboxylic acid, mercapto, and oxygenated phosphorus (eg phosphinic acid and phosphonic acid) groups.

Gray et. al., Biochemical and Biophysical Research Communication, Vol. 101, No. 4, 1981 discloses collagenase inhibitors which are α-mercaptoamides of tetrapeptides, in which the mercapto group functions as the zinc binding group. The patent publications WO 95/13289 and WO 96/11209 disclose a class of MMP inhibitors in which the zinc binding group is again an α-mercaptoamide group. MMP inhibitors having an N-formyl-N-hydroxyamino zinc binding group are also known, eg from EP-A-0236872.

BRIEF DESCRIPTION OF THE INVENTION

The present invention makes available a new class of MMP inhibitors having as zinc binding groups (i) α-mercaptoamide groups analogous to those of Gray et. al, WO 95/13289 and WO 96/11209 or (ii) an N-formyl-N-hydroxyamino group. The compounds of the invention are principally distinguished from the compounds disclosed in WO 95/13289 and WO 96/11209, and from known MMP inhibitors having the N-formyl-N-hydroxyamino zinc binding group, by having a terminal arylamide or heteroarylamide group. These structural features can confer benefits in terms of increased intrinsic activity or bioactivity as inhibitors of specific enzymes.

DETAILED DESCRIPTION OF THE INVENTION

The present invention provides compounds of general formula I

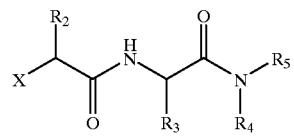

wherein

X is a group of formula (II) or (III)

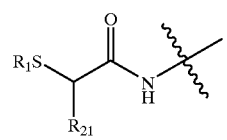

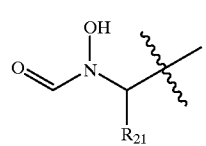

$R_2$ is a group —$(Alk)_m$—$(Q)_n$—Z wherein
m and n are independently 0 or 1,
Alk represents ($C_1$–$C_6$)alkyl, ($C_2$–$C_6$)alkenyl or ($C_2$–$C_6$)alkynyl,
Q represents —O—, —S—, —SO— or —$SO_2$—, and
Z represents hydrogen, acyl or an optionally substituted ($C_1$–$C_6$)alkyl, ($C_3$–$C_7$)cycloalkyl, ($C_2$–$C_6$)alkenyl, ($C_3$–$C_7$)cycloalkenyl, phenyl, or heterocyclyl group;

$R_1$ is hydrogen or acyl;

$R_{21}$ is (i) in the case where X is a group of formula (II), hydrogen or a group $R_2$ as defined above, or (ii) in the case where X is a group of formula (III), a group $R_2$ as defined above;

$R_3$ is the side chain of a natural or non-natural α-amino acid in which any functional groups may be protected;

$R_4$ is a phenyl or 5- or 6-membered heteroaryl ring wherein any ring nitrogen atom may be oxidised as an N-oxide, which may be optionally fused to a benzene ring or to a 5-, 6- or 7-membered heterocyclic ring, and wherein any of the rings may be optionally substituted by:
(a) one or more substituents independently selected from hydroxyl, halogen, —CN, —$CO_2H$, —$CO_2$ ($C_1$–$C_6$)alkyl, —($C_1$–$C_6$)alkyl-$CO_2$($C_1$–$C_6$)alkyl, —$CONH_2$, —CONH($C_1$–$C_6$)alkyl, —CON(($C_1$–$C_6$)alkyl)$_2$, —CHO, —$CH_2$OH, —($C_1$–$C_4$)perfluoroalkyl, —O($C_1$–$C_6$)alkyl, —S($C_1$–$C_6$)alkyl, —SO($C_1$–$C_6$)alkyl, —$SO_2$($C_1$–$C_6$)alkyl, —$NO_2$, —$NH_2$, —NH($C_1$–$C_6$)alkyl, —N(($C_1$–$C_6$)alkyl)$_2$, and —NHCO($C_1$–$C_6$)alkyl, or (b) a group selected from ($C_1$–$C_6$)alkyl, ($C_2$–$C_6$)alkenyl, ($C_2$–$C_6$)alkynyl, ($C_3$–$C_8$)cycloalkyl, ($C_4$–$C_8$)cycloalkenyl, phenyl, benzyl, heteroaryl or heteroarylmethyl any of which groups may be optionally substituted with one or more substituents selected from halogen, hydroxyl, amino, carboxyl, ($C_1$–$C_4$)perfluoroalkyl, ($C_1$–$C_6$)alkyl, —O($C_1$–$C_6$)alkyl or —S($C_1$–$C_6$)alkyl;

$R_5$ is hydrogen or a ($C_1$–$C_6$)alkyl group;

or a salt, hydrate or solvate thereof.

As used herein, the term "side chain of a natural or non-natural alpha amino acid" means the group R in a natural or non-natural amino acid of formula $H_2N$—CH(R)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

Functional groups in such amino acid side chains may be protected; for example carboxyl groups may be esterified (for example as a $C_1$–$C_6$ alkyl ester), amino groups may be converted to amides (for example as a $COC_1$–$C_6$ alkyl amide) or carbamates (for example as a C(=O)$OC_1$–$C_6$ alkyl or C(=O)$OCH_2$Ph carbamate), hydroxyl groups may be converted to ethers (for example a $C_1$–$C_6$ alkyl or a ($C_1$–$C_6$ alkyl)phenyl ether) or esters (for example a C(=O) $C_1$–$C_6$ alkyl ester) and thiol groups may be converted to thioethers (for example a tert-butyl or benzyl thioether) or thioesters (for example a C(=O)$C_1$–$C_6$ alkyl thioester).

Examples of side chains of non-natural alpha amino acids include those referred to below in the discussion of suitable $R_3$ groups for use in compounds of the present invention.

As used herein, the term "acyl" means a group $R_{20}$C(O)— where $R_{20}$ is ($C_1$–$C_6$)alkyl, ($C_2$–$C_6$)alkenyl, ($C_3$–$C_7$)cycloalkyl, phenyl, heterocyclyl, phenyl($C_1$–$C_6$)alkyl, heterocyclyl($C_1$–$C_6$)alkyl, ($C_3$–$C_7$)cycloalkyl($C_1$–$C_6$)alkyl, phenyl($C_2$–$C_6$)alkenyl, heterocyclyl($C_2$–$C_6$)alkenyl, ($C_3$–$C_7$)cycloalkyl($C_2$–$C_6$)alkenyl, any of which $R_{20}$ groups may be substituted.

As used herein, the term "heterocyclic" or "heterocyclyl" means (i) a 5–8 membered aromatic or non-aromatic heterocyclic ring containing one or more heteroatoms selected from S, N and O, and optionally fused to a benzene ring, including for example, pyrrolyl, furyl, thienyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido, 1,2-dimethyl-3,5-dioxo-1,2,4-triazolidin4-yl, 3-methyl-2,5-dioxo-1-imidazolidinyl and 3,4,4-trimethyl-2,5-dioxo-1-imidazolidinyl, or (ii) a naphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group.

As used herein, the term "heteroaryl" means a 5–7 membered aromatic heterocyclic ring containing one or more heteroatoms. Illustrative of such rings are thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

Unless otherwise specified in the context in which it occurs, the term "substituted" as applied to any moiety herein means substituted with ($C_1$–$C_6$)alkyl, ($C_1$–$C_6$) alkoxy, hydroxy, mercapto, $C_1$–$C_6$ alkylthio, oxo, amino, halo (including fluoro, chloro, bromo and iodo), trifluoromethyl, nitro, cyano, —COOH, —$CONH_2$, —CONHR$^A$ or —CONR$^A$R$^A$ wherein R$^A$ is a ($C_1$–$C_6$)alkyl group, or with phenyl or monocyclic heterocyclyl with 5–8 ring members either of which may itself be substituted with the foregoing.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

A particular sub-group of the compounds of the invention is one wherein $R_1$ is hydrogen, or a group $R_{20}$C(O)— where $R_{20}$ is ($C_1$–$C_6$)alkyl, ($C_2$–$C_6$)alkenyl, ($C_3$–$C_7$)cycloalkyl, aryl, heteroaryl, aryl($C_1$–$C_6$)alkyl, heteroaryl($C_1$–$C_6$) alkyl, ($C_3$–$C_7$)cycloalkyl($C_1$–$C_6$)alkyl, aryl($C_2$–$C_6$) alkenyl, heteroaryl($C_2$–$C_6$)alkenyl, ($C_3$–$C_7$)cycloalkyl ($C_2$–$C_6$)alkenyl, any of which $R_{20}$ groups may be substituted;

$R_{21}$ is ($C_1$–$C_6$)alkyl; ($C_2$–$C_6$)alkenyl; phenyl; substituted phenyl; phenyl ($C_1$–$C_6$)alkyl); substituted phenyl ($C_1$–$C_6$)alkyl; heterocyclyl; substituted heterocyclyl; heterocyclyl($C_1$–$C_6$)alkyl; substituted heterocyclyl ($C_1$–$C_6$)alkyl; a group BSO$_n$A— wherein n is 0, 1 or 2 and B is hydrogen or a ($C_1$–$C_6$) alkyl, phenyl, substituted phenyl, heterocyclyl, ($C_1$–$C_6$)acyl, phenacyl or substituted phenacyl group, and A represents ($C_1$–$C_6$)alkyl;aryl ($C_1$–$C_6$)alkyl; amino($C_1$–$C_6$)alkyl; hydroxy ($C_1$–$C_6$)alkyl, mercapto($C_1$–$C_6$)alkyl or carboxy ($C_1$–$C_6$)alkyl wherein the amino-, hydroxy-, mercapto- or carboxyl-group is optionally protected or the carboxyl-group amidated; lower alkyl substituted by carbamoyl, mono(lower alkyl)carbamoyl, di(lower alkyl)carbamoyl, di(lower alkyl)amino, or carboxy-lower alkanoylamino; or, only in the case where X is a group of formula (II), $R_{21}$ is hydrogen;

$R_3$ is (i) in the case where X is a group of formula (II), the side chain of a natural or non-natural α-amino acid in which any functional groups may be protected; or (ii) in the case where X is a group of formula (III), (a) a hydrocarbon group —CR$_6$R$_7$R$_8$ in which each of R$_6$, R$_7$ and R$_8$ is independently ($C_1$–$C_6$)alkyl, ($C_2$–$C_6$)alkenyl, ($C_2$–$C_6$)alkynyl, phenyl($C_1$–$C_6$) alkyl, ($C_3$–$C_8$)cycloalkyl; or R$_6$ and R$_7$ together with the carbon atom to which they are attached form a 3 to 8 membered cycloalkyl or a 5- to 6-membered heterocyclic ring; or R$_6$, R$_7$ and R$_8$ together with the carbon atom to which they are attached form a tricyclic ring (for example adamantyl); or (b) a group —CR$_9$R$_{10}$R$_{11}$ in which R$_9$ and R$_{10}$ are each independently ($C_1$–$C_6$)alkyl, ($C_2$–$C_6$) alkenyl, ($C_2$–$C_6$)alkynyl, phenyl($C_1$–$C_6$)alkyl, or a group as defined for R$_{11}$ below other than hydrogen, or R$_9$ and R$_{10}$ together with the carbon atom to which they are attached form a 3 to 8 membered cycloalkyl or a 3- to 8-membered heterocyclic ring; and $R_{11}$ is hydrogen, OH, SH, halogen, CN, $CO_2H$, $(C_1-C_4)$perfluoroalkyl, $CH_2OH$, $CO_2(C_1-C_6)$alkyl, or a —$O(C_1-C_6)$ alkyl, —$O(C_2-C_6)$ alkenyl, —$S(C_1-C_6)$ alkyl, —$SO(C_1-C_6)$alkyl, —$SO_2(C_1-C_6)$ alkyl, —$S(C_2-C_6)$ alkenyl, —$SO(C_2-C_6)$alkenyl, —$SO_2(C_2-C_6)$alkenyl; or a group —Q—W wherein Q represents a bond or —O—, —S—, —SO— or —$SO_2$— and W represents a phenyl, phenylalkyl, $(C_3-C_8)$cycloalkyl, $(C_3-C_8)$ cycloalkylalkyl, $(C_4-C_8)$cycloalkenyl, $(C_4-C_8)$ cycloalkenylalkyl, heteroaryl or heteroarylalkyl group, which group W may optionally be substituted by one or more substituents independently selected from, hydroxyl, halogen, CN, $CO_2H$, $CO_2(C_1-C_6)$alkyl, $CONH_2$, $CONH(C_1-C_6)$alkyl, $CONH(C_1-C_6$alkyl$)_2$, CHO, $CH_2OH$, $(C_1-C_4)$ perfluoroalkyl, $O(C_1-C_6)$alkyl, $S(C_1-C_6)$alkyl, $SO(C_1-C_6)$alkyl, $SO_2(C_1-C_6)$alkyl, $NO_2$, $NH_2$, $NH(C_1-C_6)$alkyl, $N((C_1-C_6)$alkyl$)_2$, NHCO$(C_1-C_6)$alkyl, $(C_1-C_6)$alkyl, $(C_2-C_6)$alkenyl, $(C_2-C_6)$alkynyl, $(C_3-C_8)$cycloalkyl, $(C_4-C_8)$ cycloalkenyl, phenyl or benzyl;

provided that when both of $R_9$ and $R_{10}$ are independently $(C_1-C_6)$alkyl, $(C_2-C_6)$alkenyl, $(C_2-C_6)$alkynyl, or phenyl $(C_1-C_6)$alkyl then $R_{11}$ is other than hydrogen;

$R_4$ is a phenyl or 5- or 6-membered heteroaryl ring wherein any ring nitrogen atom may be oxidised as an N-oxide, which may be optionally fused to a benzene ring or to a 5-, 6- or 7-membered heterocyclic ring, and wherein any of the rings may be optionally substituted by:
(a) one or more substituents independently selected from hydroxyl, halogen, —CN, —$CO_2H$, —$CO_2$ $(C_1-C_6)$alkyl, —$(C_1-C_6)$alkyl-$CO_2(C_1-C_6)$alkyl, —$CONH_2$, —$CONH(C_1-C_6)$alkyl, —$CON((C_1-C_6)$ alkyl$)_2$, —CHO, —$CH_2OH$, —$(C_1-C_4)$ perfluoroalkyl, —$O(C_1-C_6)$alkyl, —$S(C_1-C_6)$alkyl, —$SO(C_1-C_6)$alkyl, —$SO_2(C_1-C_6)$alkyl, —$NO_2$, —$NH_2$, —$NH(C_1-C_6)$alkyl, —$N((C_1-C_6)$alkyl$)_2$, and —$NHCO(C_1-C_6)$alkyl, or
(b) a group selected from $(C_1-C_6)$alkyl, $(C_2-C_6)$ alkenyl, $(C_2-C_6)$alkynyl, $(C_3-C_8)$cycloalkyl, $(C_4-C_8)$cycloalkenyl, phenyl, benzyl, heteroaryl or heteroarylmethyl any of which groups may be optionally substituted with one or more substituents selected from halogen, hydroxyl, amino, carboxyl, $(C_1-C_4)$perfluoroalkyl, $(C_1-C_6)$alkyl, —$O(C_1-C_6)$ alkyl or —$S(C_1-C_6)$alkyl;

$R_2$ is a $(C_1-C_6)$alkyl, $(C_2-C_6)$alkenyl, $(C_2-C_6)$alkynyl, phenyl$(C_1-C_6)$alkyl, heteroaryl$(C_1-C_6)$alkyl, cycloalkyl$(C_1-C_6)$alkyl or cycloalkenyl$(C_1-C_6)$ alkyl group, any one of which may be optionally substituted by one or more substituents selected from $(C_1-C_6)$ alkyl, —$O(C_1-C_6)$alkyl, —$S(C_1-C_6)$alkyl, halo and cyano (—CN);

$R_5$ is hydrogen or a $(C_1-C_6)$alkyl group;

or a salt, hydrate or solvate thereof.

There are several chiral centres in the compounds according to the invention because of the presence of asymmetric carbon atoms. The presence of several asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention wherein X is a group of formula (II), the preferred stereochemistry is in general as follows:

C atom carrying the $R_{21}$ group —S,

C atom carrying the $R_2$ group —S,

C atom carrying the $R_3$ group —S, but mixtures in which the above configurations predominate are also contemplated.

In the compounds of the invention wherein X is a group of formula (III), the preferred stereochemistry is in general as follows:

C atom carrying the $R_{21}$ group —S,

C atom carrying the $R_2$ group —R.

C atom carrying the $R_3$ group —S, but mixtures in which the above configurations predominate are also contemplated.

As previously stated, the compounds of the present invention are principally distinguished from the compounds disclosed in the prior patent publications listed above by the identity of the group $R_4$. Accordingly the groups $R_{21}$, $R_1$, $R_2$, $R_3$, and $R_5$ may include those which have been disclosed in the corresponding positions of compounds disclosed in any of the prior art patent publications listed above, or of other structurally related MMP inhibitors. Without limiting the generality of the foregoing, examples of substituents $R_{21}$, $R_1$, $R_2$, $R_3$, $R_4$, and $R_5$ are given below.

The following classes of substituent $R_3$ are suitable for use in compounds of the present invention:

$(C_1-C_6)$alkyl, benzyl, hydroxybenzyl, benzyloxybenzyl, $(C_1-C_6)$alkoxybenzyl, or benzyloxy$(C_1-C_6)$alkyl group; and the characterising group of a natural α-amino acid, in which any functional group may be protected, any amino group may be acylated and any carboxyl group present may be amidated; and a group —[Alk]$_n R_{22}$ where Alk is a $(C_1-C_6)$alkyl or $(C_2-C_6)$alkenyl group optionally interrupted by one or more —O—, or —S— atoms or —$N(R_{23})$— groups [where $R_{23}$ is a hydrogen atom or a $(C_1-C_6)$alkyl group], n is 0 or 1, and $R_{22}$ is an optionally substituted cycloalkyl or cycloalkenyl group; and a benzyl group substituted in the phenyl ring by a group of formula —$OCH_2COR_{24}$ where $R_{24}$ is hydroxyl, amino, $(C_1-C_6)$alkoxy, phenyl$(C_1-C_6)$alkoxy, $(C_1-C_6)$ alkylamino, di$((C_1-C_6)$alkyl)amino, phenyl$(C_1-C_6)$ alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; and a heterocyclic$((C_1-C_6)$alkyl group, either being unsubstituted or mono- or di-substituted in the heterocyclic ring with halo, nitro, carboxy, $(C_1-C_6)$alkoxy, cyano, $(C_1-C_6)$alkanoyl, trifluoromethyl $(C_1-C_6)$alkyl, hydroxy, formyl, amino, $(C_1-C_6)$alkylamino, di-$(C_1-C_6)$alkylamino, mercapto, $(C_1-C_6)$alkylthio, hydroxy$(C_1-C_6)$alkyl, mercapto$(C_1-C_6)$alkyl or $(C_1-C_6)$alkylphenylmethyl;

a group —$CR_a R_b R_c$ in which:

each of $R_a$, $R_b$ and $R_c$ is independently hydrogen, $(C_1-C_6)$alkyl, $(C_2-C_6)$alkenyl, $(C_2-C_6)$alkynyl, phenyl$(C_1-C_6)$alkyl, $(C_3-C_8)$cycloalkyl, the foregoing being subject to the proviso that $R_a$, $R_b$ and $R_c$ are not all hydrogen; or $R_c$ is hydrogen, $(C_1-C_6)$alkyl, $(C_2-C_6)$alkenyl, $(C_2-C_6)$ alkynyl, phenyl$(C_1-C_6)$alkyl, or $(C_3-C_8)$cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently $(C_1-C_6)$alkyl, $(C_2-C_6)$alkenyl, $(C_2-C_6)$alkynyl, phenyl$(C_1-C_6)$ alkyl, or a group as defined for $R_c$ below other than hydrogen, or $R_a$ and $R_b$ together with the carbon atom to which they are attached form a 3 to 8 membered cycloalkyl or a 3- to 8-membered heterocyclic ring, and $R_c$ is hydrogen, —OH, —SH, halogen, —CN, —CO$_2$H, $(C_1-C_4)$perfluoroalkyl, —CH$_2$OH, —CO$_2$(C$_1$–C$_6$)alkyl, —O(C$_1$–C$_6$)alkyl, —O(C$_2$–C$_6$)alkenyl, —S(C$_1$–C$_6$)alkyl, —SO(C$_1$–C$_6$)alkyl, —SO$_2$(C$_1$–C$_6$) alkyl, —S(C$_2$–C$_6$) alkenyl, —SO(C$_2$–C$_6$)alkenyl, —SO$_2$(C$_2$–C$_6$) alkenyl or a group —Q—W wherein Q represents a bond or —O—, —S—, —SO— or —SO$_2$— and W represents a phenyl, phenylalkyl, $(C_3-C_8)$cycloalkyl, $(C_3-C_8)$cycloalkylalkyl, $(C_4-C_8)$cycloalkenyl, $(C_4-C_8)$cycloalkenylalkyl, heteroaryl or heteroarylalkyl group, which group W may optionally be substituted by one or more substituents independently selected from, hydroxyl, halogen, —CN, —CO$_2$H, —CO$_2$(C$_1$–C$_6$)alkyl, —CONH$_2$, —CONH(C$_1$–C$_6$) alkyl, —CONH(C$_1$–C$_6$alkyl)$_2$, —CHO, —CH$_2$OH, $(C_1-C_4)$perfluoroalkyl, —O(C$_1$–C$_6$)alkyl, —S(C$_1$–C$_6$)alkyl, —SO(C$_1$–C$_6$)alkyl, —SO$_2$(C$_1$–C$_6$)alkyl, —NO$_2$, —NH$_2$, —NH(C$_1$–C$_6$)alkyl, —N((C$_1$–C$_6$)alkyl)$_2$, —NHCO(C$_1$–C$_6$)alkyl, $(C_1-C_6)$alkyl, $(C_2-C_6)$alkenyl, $(C_2-C_6)$alkynyl, $(C_3-C_8)$cycloalkyl, $(C_4-C_8)$cycloalkenyl, phenyl or benzyl.

Examples of particular $R_{21}$ groups suitable for inclusion in the compounds of the invention include hydrogen, methyl, ethyl, n-propyl, n-, iso- or tert-butyl, phenyl, benzyl, 4-hydroxybenzyl, allyl, thienylsulphanylmethyl, thienylsulphinylmethyl, thienylsulphonylmethyl. Also included are heterocyclyl-(CH$_2$)$_n$— groups wherein n is 1, 2, 3 or 4, and the heterocyclyl group is phthalimido, 1,2-dimethyl-3,5-dioxo-1,2,4-triazolidin-4-yl, 3-methyl-2,5-dioxo-1-imidazolidinyl, 3,4,4-trimethyl-2,5-dioxo-1-imidazolidinyl, naphththalimido (ie 1,3-dihydro-1,3-dioxo-2H-benz[f]isoindol-2-yl), 1,3-dihydro-1-oxo-2H-benz[f] isoindol-2-yl, 1,3-dihydro-1,3-dioxo-2H-pyrrolo[3,4-b] quinolin-2-yl, or 2,3-dihydro-1,3-dioxo-1H-benz[d,e] isoquinolin-2-yl. Presently preferred are compounds in which $R_{21}$ is n-propyl, phthalimidopropyl, phthalimidobutyl, phthalimidoethyl, phthalimidomethyl, 3,4,4-trimethyl-2,5-dioxo-1-imidazolidinylpropyl, 3,4,4-trimethyl-2,5-dioxo-1-imidazolidinyethyl, 3,4,4-trimethyl-2,5-dioxo-1-imidazolidinylmethyl.

Examples of particular $R_1$ groups suitable for inclusion in the compounds of the invention include hydrogen, and groups $R_{20}C(O)$— where $R_{20}$ is a $(C_1-C_6)$alkyl group such as methyl or ethyl.

Examples of particular $R_2$ groups suitable for inclusion in the compounds of the invention include $C_1$–$C_{12}$ alkyl which may be interrupted by —O— or —S—; or $C_3$–$C_6$ alkenyl, or $C_3$–$C_6$ alkynyl; or phenyl$(C_1-C_6$ alkyl)-, phenoxy$(C_1-C_6$ alkyl)-, or phenylthio$(C_1-C_6$ alkyl)-, the alkyl moiety of any of which may be interrupted by —O— or —S— and the phenyl group of any of which may be substituted by halogen, $C_1-C_6$ alkyl, $C_1-C_6$ alkoxy or phenyl; or phenyl$(C_2-C_6$ alkenyl)-, or phenyl$(C_2-C_6$ alkynyl)-, phenoxy$(C_2-C_6$ alkenyl)-, phenoxy$(C_2-C_6$ alkynyl)-, phenylthio$(C_2-C_6$ alkenyl)-, or phenylthio$(C_2-C_6$ alkynyl)-, any of which may be substituted in the phenyl ring by halogen, $C_1-C_6$ alkyl, $C_1-C_6$ alkoxy or phenyl.

Specific examples of such groups include iso-butyl, n-pentyl, n-hexyl, n-heptyl, n-octyl, n-nonyl, n-decyl, 2-methylthioethyl, 2-ethylthioethyl, ethylthiomethyl, propylthiomethyl, butylthiomethyl, phenylpropyl, 4-chlorophenylpropyl, 4-methylphenylpropyl, 4-methoxyphenylpropyl, 2-benzylthioethyl, benzylthiomethyl, 4-phenyl-phenylpropyl, 4-(pyridin-4-yl) phenylpropyl, 4-phenylbenzylthiomethyl, 3-(4-phenylphenyl)prop-2-ynyl, and phenoxybutyl. Presently preferred are compounds in which $R_2$ is iso-butyl, 2-methylthioethyl, n-octyl, benzyloxypropyl, phenoxybutyl, 4-phenylphenylpropyl, 4-(pyridin-4-yl)phenylpropyl, or 4-phenylbenzylthiomethyl.

Examples of particular $R_3$ groups suitable for inclusion in the compounds of the invention include benzyl, 4-chlorophenylmethyl, 2-thienylmethyl, iso-butyl or t-butyl, 1-benzylthio-1-methylethyl, and 1-mercapto-1-methylethyl. Presently preferred are compounds in which $R_3$ is benzyl, t-butyl or 1-mercapto-1-methylethyl.

Examples of particular $R_4$ groups suitable for inclusion in the compounds of the invention include optionally substituted phenyl, furanyl, thienyl, pyrrolinyl, tetrahydrofuranyl, imidazolyl, oxadiazolyl, thiazolyl, thiadiazolyl, pyridinyl, pyridinyl N-oxides, piperazinyl, indolyl, pyrazinyl, pyridazinyl, pyrimidinyl, dithianyl, isoxazolyl or quinolinyl. Examples of particular $R_4$ groups include phenyl, 2-methoxyphenyl, 3-methoxyphenyl, 4-methoxyphenyl, 3,4-dimethoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-t-butylphenyl, 3-t-butylphenyl, 4-t-butylphenyl, 4-t-butyl-2,6-dimethylphenyl, 2-nitrophenyl, 3-nitrophenyl, 4-nitrophenyl, 2-cyanophenyl, 3-cyanophenyl, 4-cyanophenyl, 2-acetylphenyl, 3-acetylphenyl, 4-acetylphenyl, 2-methylsulphonylphenyl, 3-methylsulphonylphenyl, 4-methylsulphonylphenyl, 2-trifluoromethylphenyl, 3-trifluoromethylphenyl, 4-trifluoromethylphenyl, 3,5-ditrifluoromethylphenyl, 2-aminophenyl, 3-aminophenyl, 4-aminophenyl, 2-N,N-dimethylaminophenyl, 3-N,N-dimethylaminophenyl, 4-N,N-dimethylaminophenyl, 2-hydroxyphenyl, 3-hydroxyphenyl, 4-hydroxyphenyl, furan-2-yl, thien-2-yl, pyrrol-2-yl, tetrahydrofuran-2-yl, imidazol-2-yl, thiazol-2-yl, 4-ethoxycarbonylmethylthiazol-2-yl, 4-phenylthiazol-2-yl, 4,5-dimethylthiazol-2-yl, 5-bromothiazol-2-yl, 4-tert-butylthiazol-2-yl, benzothiazol-2-yl, 1,2,4-oxadiazol-5-yl, 3-methyl-1,2,4-oxadiazol-5-yl, 3-phenyl-1,2,4-oxadiazol-5-yl, 1,2,4-oxadiazol-3-yl, 1,3,4-oxadiazol-2-yl, 1,2,4-thiadiazol-5-yl, 3-phenyl-1,2,4-thiadiazol-5-yl, 1,3,4-thiadiazol-2-yl, 5-methyl-1,3,4-thiadiazol-2-yl, pyridin-2-yl, pyridin-3-yl, pyridin-4-yl, N-oxides of pyridin-2-yl pyridin-3-yl and pyridin-4-yl, piperazin-1-yl, indol-2-yl, benzimidazol-2-yl, benzotriazol-2-yl, pyrazin-2-yl, 1,2-pyridazin-3-yl, 1,3-pyrimidin-5-yl, 1,3-dithian-2-yl, benzo[f]thien-2-yl, isoxazol-5-yl, quinolin-3-yl. Presently preferred are compounds in which $R_4$ is phenyl, 3-methoxyphenyl, pyridin-2-yl, pyridin-3-yl, pyridin-4-yl, and thiazol-2-yl, 4,5-dimethylthiazol-2-yl, 5-bromothiazol-2-yl, 4-ethoxycarbonylmethylthiazol-2-yl, 5-methyl-1,3,4-thiadiazol-2-yl, 4-tertbutylthiazol-2-yl, or quinolin-3-yl. Particularly preferred at present are compounds wherein $R_4$ is 3-methoxyphenyl, pyridin-2-yl, pyridin-3-yl, pyridin-4-yl, thiazol-2-yl, 4-ethoxycarbonylmethylthiazol-2-yl, 5-methyl-1,3,4-thiadiazol-2-yl and 4-tert-butylthiazol-2-yl.

Examples of particular $R_5$ groups include hydrogen, methyl and ethyl. Presently preferred are compounds in which $R_5$ is hydrogen.

Interesting compounds of the invention are:

2R or S-mercapto-pentanoic acid {3-methyl-1S-[2-phenyl-1S-(thiazol-2-ylcarbamoyl)-ethylcarbamoyl]-butyl}amide;

2R or S-mercapto-hexanoic acid {3-methyl-1S-[1S-(thiazol-2-ylcarbamoyl)-2-thiophen-2-yl-ethylcarbamoyl]-butyl}amide;

2R or S-mercapto-hexanoic acid {3-methyl-1S-[2-phenyl-1S-(pyridin-3-ylcarbamoyl)-ethylcarbamoyl]-butyl}amide;

2R or S-mercapto-hexanoic acid {1S-[2-(4-chloro-phenyl)-1S-(quinolin-8-ylcarbamoyl)-ethylcarbamoyl]-3-methyl-butyl}amide;

thioacetic acid 1S-{1S-[2-phenyl-1S-(pyridin-3-ylcarbamoyl)-ethylcarbamoyl]-3-methyl-butylcarbamoyl}-4-(1,3-dioxo-1,3-dihydro-isoindol-2-yl)-butyl ester;

5-(1,3-dioxo-1,3-dihydro-isoindol-2-yl)-2S-mercaptopentanoic acid {3-methyl-1S-[2-phenyl-1S-(pyridin-3-ylcarbamoyl)-ethylcarbamoyl]-butyl}-amide;

thioacetic acid 1S-{1S-[2,2-dimethyl-1S-(pyridin-2-ylcarbamoyl)-propylcarbamoyl]-3-methyl-butylcarbamoyl}-4-(1,3-dioxo-1,3-dihydro-isoindol-2-yl)-butyl ester;

5-(1,3-dioxo-1,3-dihydro-isoindol-2-yl)-2S-mercaptopentanoic acid {S-[2,2-dimethyl-1S-(pyridin-2-ylcarbamoyl)-propylcarbamoyl]-3-methyl-butyl}-amide;

thioacetic acid 1S-{1S-[2-phenyl-1S-(pyridin-4-ylcarbamoyl)-ethylcarbamoyl]-3-methyl-butylcarbamoyl}-4-(1,3-dioxo-1,3-dihydro-isoindol-2-yl)-butyl ester;

5-(1,3-dioxo-1,3-dihydro-isoindol-2-yl)-2S-mercaptopentanoic acid {3-methyl-1S-[2-phenyl-1S-(pyridin-4-ylcarbamoyl)-ethylcarbamoyl]-butyl}amide;

thioacetic acid 1S-{1S-[2,2-dimethyl-1S-(pyridin-2-ylcarbamoyl)-propylcarbamoyl]-3-methyl-butylcarbamoyl}-5-(1,3-dioxo-1,3-dihydro-isoindol-2-yl)-pentyl ester;

6-(1,3-dioxo-1,3-dihydro-isoindol-2-yl)-2S-mercaptohexanoic acid {1S-[2,2-dimethyl-1S-(pyridin-2-ylcarbamoyl)-propylcarbamoyl]-3-methyl-butyl}amide;

thioacetic acid 1S-{1S-[2,2-dimethyl-1S-(thiazol-2-ylcarbamoyl)-propylcarbamoyl]-3-methyl-butylcarbamoyl}-4-(1,3-dioxo-1,3-dihydro-isoindol-2-yl)-butyl ester;

5-(1,3-dioxo-1,3-dihydro-isoindol-2-yl)-2S-mercaptopentanoic acid {1S-[2,2-dimethyl-1S-(pyridin-4-ylcarbamoyl)-propylcarbamoyl]-3-methyl-butyl}-amide;

thioacetic acid 1S-{1S-[2,2-dimethyl-1S-(pyridin-4-ylcarbamoyl)-propylcarbamoyl]-3-methyl-butylcarbamoyl}-4-(1,3-dioxo-1,3-dihydro-isoindol-2-yl)-butyl ester;

thioacetic acid 1S-{1S-[2,2-dimethyl-1S-(pyridin-2-ylcarbamoyl)-propylcarbamoyl]-3-methylthio-propylcarbamoyl}-5-(1,3-dioxo-1,3-dihydro-isoindol-2-yl}-pentyl ester;

6-(1,3-dioxo-1,3-dihydro-isoindol-2-yl)-2S-mercaptohexanoic acid {1S-[2,2-dimethyl-1S-(pyridin-4-ylcarbamoyl)-propylcarbamoyl]-3-methyl-butyl}amide;

thioacetic acid 1S-{2-(biphenyl-4-ylmethylthio)-1S-[2,2-dimethyl-1S-(pyridin-4-ylcarbamoyl)-propylcarbamoyl]-ethylcarbamoyl}-4-(1,3-dioxo-1,3-dihydro-isoindol-2-yl}butyl ester;

5-(1,3-dioxo-1,3-dihydro-isoindol-2-yl)-2S-mercaptopentanoic acid {2-(biphenyl-4-ylmethylthio)-1S-[2,2-dimethyl-1S-(pyridin-4-ylcarbamoyl)-propylcarbamoyl]-ethyl}amide;

and salts, hydrates and solvates thereof.

Further specific compounds of the invention, accessible by methods analogous to those described in the examples below, are:

thioacetic acid S-[1S-{4-biphenyl-4-yl-1S-[2,2-dimethyl-1S-(pyridin-4-ylcarbamoyl)-propylcarbamoyl]-butylcarbamoyl}-4-(3,4,4-trimethyl-2,5-dioxo-imidazolidin-1-yl)-butyl]ester;

2S-mercapto-5-(3,4,4-trimethyl-2,5-dioxo-imidazolidin-1-yl) pentanoic acid 4-{biphenyl-4-yl-1S-[2,2-dimethyl-1S-(pyridin-4-ylcarbamoyl)-propylcarbamoyl]-butyl}amide;

2S-mercapto-5-(3,4,4-trimethyl-2,5-dioxo-imidazolidin-1-yl) pentanoic acid [1S-[2,2-dimethyl-1S-(pyridin-4-ylcarbamoyl)-propylcarbamoyl]-4-(9H-fluoren-2-yl)-butyl]amide;

2S-mercapto-5-(3,4,4-trimethyl-2,5-dioxo-imidazolidin-1-yl) pentanoic acid 3-{biphenyl-4-yl-1S-[2,2-dimethyl-1S-(pyridin-2-ylcarbamoyl)-propylcarbamoyl]-propyl}amide;

2S-mercapto-5-(3,4,4-trimethyl-2,5-dioxo-imidazolidin-1-yl) pentanoic acid 2-{biphenyl-4-yl-1S-[2,2-dimethyl-1S-(pyridin-2-ylcarbamoyl)-propylcarbamoyl]-ethyl}amide;

2S-mercapto-5-(3,4,4-trimethyl-2,5-dioxo-imidazolidin-1-yl) pentanoic acid {1S-[2,2-dimethyl-1S-(pyridin-2-ylcarbamoyl)-propylcarbamoyl]-3-methyl-butyl}amide;

thioacetic acid S-[1S-{1S-[2,2-dimethyl-1S-(pyridin-4-ylcarbamoyl)-propylcarbamoyl]-3-methyl-butylcarbamoyl}-4-(3,4,4-trimethyl-2,5-dioxo-imidazolidin-1-yl)butyl]ester;

2S-mercapto-5-(3,4,4-trimethyl-2,5-dioxo-imidazolidin-1-yl) pentanoic acid {1S-[2,2-dimethyl-1S-(pyridin-3-ylcarbamoyl)-propylcarbamoyl]-3-methyl-butyl}amide;

3R&S-(formyl-hydroxy-amino)-2R-isobutyl-6-(3,4,4-trimethyl-2,5-dioxo-imidazolidin-1-yl)-hexanoic acid [2,2-dimethyl-1S-(pyridin-4-ylcarbamoyl)-propyl]amide;

6-(1,3-dioxo-1,3-dihydro-isoindol-2-yl)-3R&S-(formyl-hydroxy-amino)-2R-isobutyl hexanoic acid [2,2-dimethyl-1S-(pyridin-4-ylcarbamoyl)-propyl]amide.

5-(1,3-dioxo-1,3-dihydro-isoindol-2-yl)-3R&S-(formyl-hydroxy-amino)-2R-isobutyl pentanoic acid [2,2-dimethyl-1S-(pyridin-2-ylcarbamoyl)-propyl]amide.

Compounds according to the present invention in which X is a group of formula (II) and $R_1$ is hydrogen may be prepared by a process comprising deprotecting the protected thiol group in a compound of formula (IV)

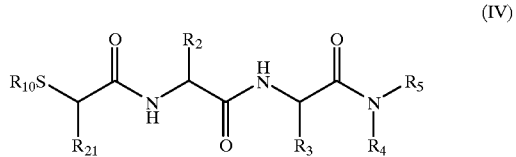

(IV)

wherein $R_{10}$ is a thiol protecting group $R_2$, $R_3$, $R_4$, $R_5$, and $R_{21}$ are as defined in formula (I) except that any functional groups in $R_2$, $R_3$, $R_4$, $R_5$, and $R_{21}$ may be protected, and after or together with deprotection of the protected thiol group, any protected functional groups in $R_2$, $R_3$, $R_4$, $R_5$, and $R_{21}$ are also deprotected. Suitable thiol protecting groups for use in the above process include benzyl and tert-butyl, but others which are suitable are known from the art of peptide synthesis, see for example "Protective Groups in Organic Synthesis", by Greene and Wuts, and "The Practice of Peptide Synthesis" by Bodanszki et al. Protecting groups for other functional groups which may be present in $R_2$, $R_3$, $R_4$, $R_5$, and $R_{21}$ are also known from those publications and from the art of peptide synthesis generally. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Compounds of formula (IV) may be prepared by coupling a carboxylic acid of formula (V) with an amine of formula (VI)

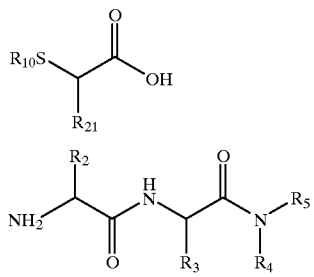

(V)

wherein $R_{10}$, $R_2$, $R_3$, $R_4$, $R_5$, and $R_{21}$ are as described above in relation to formula (IV). This coupling reaction may be carried out by conversion of (V) to an activated derivative such as the pentafluorophenyl, hydroxysuccinyl, or hydroxybenzotriazolyl ester by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ), followed by reaction of the activated ester with (VI). In the case where $R_{10}$ in compound (V) is a group of formula $R_{20}CO$ as defined in relation to group $R_1$ of formula (I), the product to the above coupling reaction is of course a compound of the invention of formula (I) in which $R_1$ is other than hydrogen.

Amine intermediates of formula (VI) are either known compounds or may be prepared from known amino acid starting materials using standard methods and by analogy with the specific preparative examples herein. Substituted 2-mercapto carboxylic acids (V) are known or are accessible by methods analagous to those used for such intermediates in the specific examples herein.

Compounds of the invention in which X is a group of formula (III) may be prepared by deprotecting an N-protected N-formyl-N-hydroxyamino compound of formula (VII):

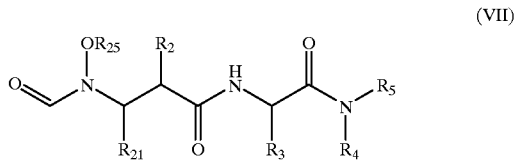

(VII)

in which $R_{21}$, $R_2$, $R_3$, $R_4$, and $R_5$ are as defined in general formula (I) and $R_{25}$ is a group convertible to a hydroxy group by hydrogenolysis or hydrolysis. Benzyl is a preferred $R_{25}$ group for removal by hydrogenolysis, and tetrahydropyranyl is a preferred group for removal by acid hydrolysis.

Compounds of formula (VII) may be prepared by a process comprising: causing an acid of formula (VIII) or an activated derivative thereof to react with an amine of formula (IX)

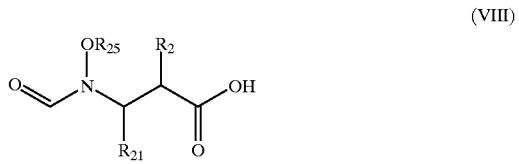

(VIII)

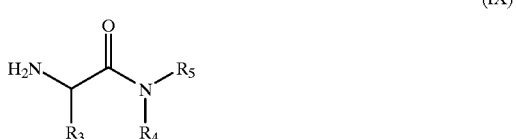

(IX)

wherein $R_{21}$ $R_2$, $R_3$, $R_4$, and $R_5$ are as defined in general formula (I) except that any substituents in $R_{21}$, $R_2$, $R_3$, $R_4$, and $R_5$ which are potentially reactive in the coupling reaction may themselves be protected from such reaction, and $R_{25}$ is a group convertible to a hydroxy group by hydrogenolysis or hydrolysis as referred to in connection with formula (VII) above, and optionally removing protecting groups from $R_{21}$, $R_2$, $R_3$, $R_4$, and $R_5$.

Compounds of formula (VIII) may be prepared by N-formylation, for example using acetic anhydride and formic acid, of compounds of formula (X)

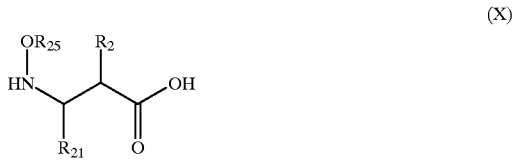

(X)

wherein $R_{21}$, $R_2$ and $R_{25}$ are as defined in relation to formula (VII).

As mentioned above, compounds of formula (I) are useful in human or veterinary medicine since they are active as inhibitors of MMPs.

Accordingly in another aspect, this invention concerns:
(i) a method of management (by which is meant treatment or prophylaxis) of diseases or conditions mediated by MMPs in mammals, in particular in humans, which method comprises administering to the mammal an effective amount of a compound as defined with respect to formula (I) above, or a pharmaceutically acceptable salt thereof; and
(ii) a compound as defined with respect to formula (I) for use in human or veterinary medicine, particularly in the management (by which is meant treatment or prophylaxis) of diseases or conditions mediated by MMPs; and
(iii) the use of a compound as defined with respect to formula (I) in the preparation of an agent for the management (by which is meant treatment or prophylaxis) of diseases or conditions mediated by MMPs.

Diseases or conditions mediated by MMPs include those involving tissue breakdown such as bone resorption, inflammatory diseases, dermatological conditions, tumour growth and vascularisation, and tumour invasion by secondary metastases, in particular rheumatoid arthritis, osteoarthritis, periodontitis, gingivitis, corneal ulceration and tumour invasion by secondary metastases.

In a further aspect of the invention there is provided a pharmaceutical or veterinary composition comprising a compound of formula (I) together with a pharmaceutically or veterinarily acceptable excipient or carrier. In view of the oral bioavailability advantages of compounds in accordance with the invention, a further aspect of the invention comprises a pharmaceutical or veterinary composition comprising a compound of formula (I) together with a pharmaceutically or veterinarily acceptable excipient or carrier, characterised in that the composition is adapted for oral administration.

One or more compounds of general formula (I) may be present in the composition together with one or more excipient or carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 25 to 250 mg of a compound of the invention. A suitable daily dose for a mammal may vary widely depending on the condition of the patient.

However, a dose of a compound of general formula I of about 0.1 to 300 mg/kg body weight, particularly from about 1 to 100 mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint. The daily dosage for a 70 kg mammal may be in the range 10 mgs to 1 gram.

The following Examples illustrate embodiments of the invention:

The amino acids used in the examples were commercially available or were prepared according to literature procedures.

The following abbreviations have been used throughout:

Boc tert-Butyloxycarbonyl

DMAP 4-Dimethylaminopyridine

DMF N,N-Dimethylformamide

DIPCDI Diisopropylcarbodiimide

EDC N-Ethyl-N'-(3-dimethylaminopropyl)carbodiimide hydrochloride

Fmoc 9-Fluorenylmethyloxycarbonyl

HMBA 4-(Hydroxymethyl)benzoic acid

HOBt 1-Hydroxybenzotriazole

MBHA 4-Methylbenzhydrylamine

NMM N-Methylmorpholine

TFA Trifluoroacetic acid

Thi 2-Thienylalanine $^1$H and $^{13}$C NMR spectra were recorded using a Bruker AC 250E spectrometer at 250.1 and 62.9 MHz, respectively.

EXAMPLE 1

2RS-Mercaptohexanoic acid {3-methyl-1S-[2-phenyl-1S-(thiazol-2-ylcarbamoyl)-ethylcarbamoyl]-butyl}-amide

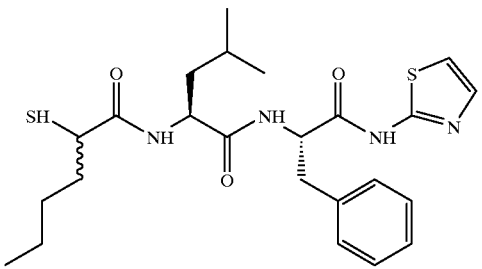

(a) Boc-S-phenylalanine (275 mg, 1.04 mmol), HOBt (172 mg) and 2-aminothiazole (114 mg) were dissolved in dichloromethane (25 ml). EDC (218. mg) was added and the reaction mixture was stirred overnight. Saturated aq. NaHCO₃ was added and the organics were extracted, washed with 1 M HCl and brine dried (anhydrous MgSO₄) and filtered. The solvents were removed to provide Boc-Phe-NH-(2-thiazole). ¹H-nmr; δ(CDCl₃), 7.58 (1H, d), 7.22 - 7.12 (5H, m), 7.09 (1H, m), 6.92 (1 H, d), 4.32 (1H, m), 3.12 (2H, dd) and 1.48 (9H, s).

(b) A saturated solution of HCl gas in ethyl acetate was added to the above amide at 0° C. After 30 minutes at room temperature the solvent was evaporated. Boc-S-leucine (250 mg) and HOBt (167 mg) were added in dichloromethane (60 ml). NMM was added followed by EDC (210 mg). The solution was stirred for 2 hours before purification as in (a) to give Boc-Leu-Phe-NH-(2-thiazole) as a brown solid after drying under high vacuum. ¹H-nmr; δ(CDCl₃), 7.53 (1 H, d), 7.32- 7.21 (6H, m), 7.01 (1 H, d), 5.72 (1 H, m), 5.32 (1H, m), 4.22 (I H, m), 3.21 (2H, m), 1.70- 1.52 (3H, m), 1.48 (9H, s) and 0.92 (6H, d).

(c) The above amide was N-deprotected as described in (b) and the resulting gum was treated with 2RS-thioacetyl-hexanoic acid (218 mg)(prepared as in WO 95/13289) HOBt (173 mg) and EDC (200 mg) in dichloromethane for 2 hours. The mixture was processed as in (a) to afford n-propyl-CH(SAc)-CO-Leu-Phe-NH-(2-thiazole) as a 1:1 mixture of diastereoisomers. ¹H-nmr; δ(CDCl₃), 8.02 (1H, m), 7.72 -7.48 (3H, m), 7.15 (5H, m), 7.02 (1H, dd), 5.50 (1H, m), 4.55 (11 H, m), 4.02 (1H, m), 3.12 (2H, m), 2.25 (1.5H, s), 2.13 (1.5H, s), 1.75 - 1.22 (9H, m) and 0.93 - 0.72 (9H, m).

(d) The above mixture of diastereoisomeric thioacetates was placed under argon and dissolved in 2:1 methanol/conc. ammonia solution (250 ml). After stirring for 2 hours the reaction mixture was acidified to pH 2.0 with 1M HCl and extracted with dichloromethane (3×50 ml). The combined extracts were dried (anhydrous MgSO₄), filtered and evaporated to leave a gum. Flash chromatography (silica gel, 3% methanol in dichloromethane) gave the desired thiol as a white solid. ¹H-nmr; δ(CDCl₃), 7.82 (1H, m), 7.52 (1 H, m), 7.21 (5H, br s), 7.11 (1 H, dd), 5.02 (1 H, br m), 4.52 (1 H, br m), 4.21 - 3.94 (3H, m), 3.32 - 3.12 (3H, m), 1.91 - 1.31 (9H, m) and 0.93 - 0.78 (9H, m).

The following additional compounds of Examples 2–4 were prepared according to the methods of Example 1:

EXAMPLE 2

2RS-Mercapto-hexanoic acid {3-methyl-1S-[1S-(thiazol-2-ylcarbamoyl)-2-thiophen-2-yl-ethylcarbamoyl]-butyl}-amide

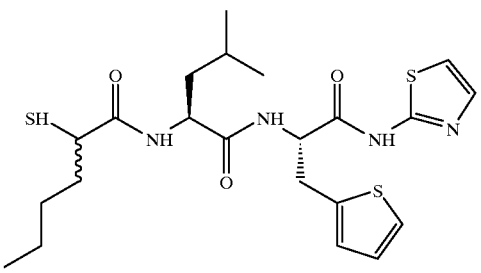

1H-nmr; δ(CDCl₃), 7.88 (1 H, d), 7.82 (1 H, d), 7.42 - 7.32 (2H, d), 7.28 (1 H, dd), 7.11 (1H, m), 7.03 (1H, dd), 6.83 (1H, m), 4.36 (1H, m), 4.08 (1 H, t), 3.25 (3H, m), 1.94 -1.21 (9H, m) and 0.95 - 0.76 (9H, m).

EXAMPLE 3

2RS-Mercapto-hexanoic acid {3-methyl-1S-[2-phenyl-1S-(pyridin-3-ylcarbamoyl)-ethylcarbamoyl]-butyl}-amide

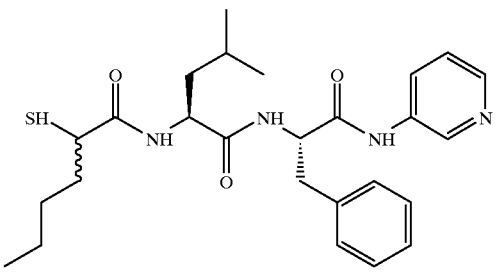

¹H-nmr; δ(CDCl₃), 7.78 (1H, dd), 7.62 (1H, dd), 7.44 (1H, dt), 7.36 (1H, dt), 7.12 (5H, br s), 4.61 (1H, m), 4.26 (1H, m), 3.12-3.04 (2H, m), 1.78-1.12 (10 H, m) and 0.94 - 0.65 (9H, m).

EXAMPLE 4

2RS-Mercaptohexanoic acid {1 S-[2-(4-chloro-phenyl)-1S-(quinolin-8-ylcarbamoyl)-ethylcarbamoyl]-3-methyl-butyl}-amide

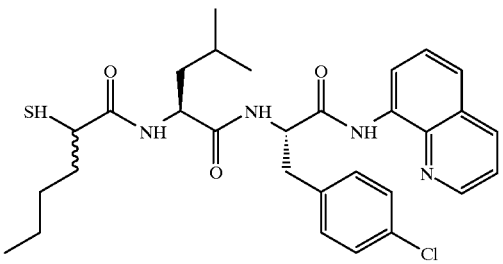

¹H-nmr; δ(CDCl₃), 8.60 (1 H, m), 8.21 (1 H, m), 7.96 -7.45 (4H, m), 7.40 (2H, m), 7.15 (1H ,s), 7.10 (1H, m), 4.62 (1H, m), 4.38 (1H, m), 4.02 (1H, m), 3.6 (1H, m), 3.02 (2H, m), 1.87 - 1.12 (9H, m) and 0.95 - 0.78 (9H, m).

EXAMPLE 5

Thioacetic acid 1S-{1S-[2-phenyl-1S-(pyridin-3-ylcarbamoyl)-ethylcarbamoyl]-3-methyl-butylcarbamoyl}-4-(1,3-dioxo-1,3-dihydro-isoindol-2-yl)-butyl ester

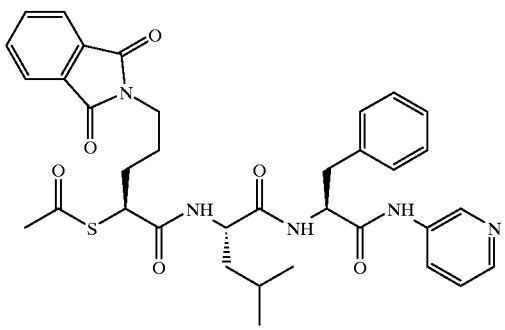

Boc-Phenylalanine (1.00 g, 3.77 mmol) and 3-aminopyridine (350 mg, 3.72 mmol) were dissolved in DMF (20 ml). HATU (1.46g, 3.72 mmol) was added followed by diisopropylethylamine (1.31 ml, 7.5 mmol). The resulting yellow solution was then stirred at room temperature for 24 h before the solvent was removed in vacuo, the residue dissolved in ethyl acetate and washed successively with 1 M potassium hydrogen sulfate, saturated sodium bicarbonate and brine solutions. After drying (MgSO$_4$) the solvent was removed to leave the Boc-protected amide as a white solid (1.24 g), essentially pure by tlc and nmr.

This amide (480 mg) was dissolved in a saturated solution of hydrogen chloride in ethyl acetate (30 ml) at 0° C. for 45 minutes. The solution was then evaporated to dryness and Boc-leucine hydrate (380 mg) and hydroxybenzotriazole (250 mg) added. The solids were dissolved in DMF (20 ml) and WSCDI (307 mg) was added along with N-methylmorpholine (190 μL). The solution was stirred at room temperature overnight before the solvent was evaporated and the residue treated as above to give the Boc-dipeptide amide as a pale yellow crisp foam (580 mg) sufficiently pure to use without any purification.

The Boc group was removed from the dipeptide (340 mg) in the manner described above. 5-Phthalimido-2S-acetylmercaptopentanoic acid (264 mg) and N-hydroxyazabenzotriazole (112 mg) were added and the mixture was dissolved in DMF (20 ml). WSCDI (158 mg) was added followed by NMM (271 μL) and the solution was then stirred for 24 h before workup in the manner described above. The crude thioacetate was purified by column chromatography (SiO$_2$, 1–3% methanol in dichloromethane) to give the product as a white solid (288 mg).

$^1$H nmr (CDCl$_3$); 0.81 (3H, d, J=6.0 Hz, Leu), 0.89 (3H, d, J=6.0 Hz, Leu), 1.33–1.87 (7H, m), 2.40 (3H, s, SCOCH$_3$), 3.25 (1H, dd, J=8.9 and 14.2 Hz, CH$_a$H$_b$Ph), 3.46 (1H, dd, J=5.4 and 14.2 Hz, CH$_a$CH$_b$Ph), 3.66 (2H, m), 4.13 (2H, m), 4.91 (1H, m), 6.63 (1 H, d, J=4.5 Hz), 6.72 (1 H, d, J=8.4 Hz, py), 7.22 (1 H, m), 7.27 (5 H, m, Ph), 7.70 (2H, m, phth), 7.82 (2H, m, phth), 8.10 (1H, br dd, J=8.4 Hz, py), 8.28 (1H, dd, J=1.4 & 4.5 Hz, py), 8.51 (1H, brs) and 8.76 (1H, d, J=2.3 Hz).

$^{13}$C nmr (CDCl$_3$); 21.1, 22.8, 24.6, 25.4, 26.1, 26.4, 30.3, 36.2, 36.6, 39.8, 53.9, 54.2, 123.3, 126.7, 126.9, 128.6, 129.0, 131.6, 134.1, 134.2, 134.6, 136.8, 141.3, 144.9, 168.4, 169.6, 171.5, 172.5, and 197.5.

$\upsilon_{max}$ cm$^{-1}$ (KBr) 1770, 1713 (vs), 1651 (s) and 1538.

EXAMPLE 6

5-(1,3-Dioxo-1,3-dihydro-isoindol-2-yl)-2S-mercaptopentanoic acid {3-methyl-1S-[2-phenyl-1S-(pyridin-3-ylcarbamoyl)-ethylcarbamoyl]-butyl}amide

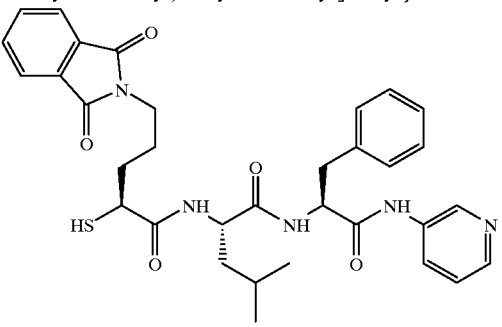

Sodium hydroxide (0.8 ml of a 0.42 M soln) was added under argon to a cooled solution in methanol (20 ml) of the thioacetate from Example 1 (220 mg) and mercaptoethanol (250 μL). After 20 minutes tlc analysis indicated that the starting material had been consumed. Acetic acid (0.8 ml) was added and the solvent evaporated to leave a gum which was triturated with ether to give a white solid. Residual solvent and mercaptoethanol were removed by decantating and the pure thiol was obtained by flash chromatography on silica (1–5% methanol in dichloromethane). Reverse phase Hplc indicated the purity as >96%.

$^1$H nmr (CDCl$_3$); 0.89 (3H, d, J=5.7 Hz, Leu), 0.94 (3H, d, J=5.7 Hz), 1.48–1.91 (7H, m), 2.89 (1 H, t, J=5.8 Hz), 3.21 (1 H, d, J=6.5 Hz), 3.35 (1 H, m), 3.69 (2H, m, CH$_2$N), 3.92 (1 H, t, J=5.8 Hz), 4.29 (1 H, m), 4.84 (1 H, dd, J=6.9 and 14.5 Hz), 6.75 (2H, m, NH), 7.23 (6H, m, Ph and py), 7.71 (2H, m, phth), 7.83 (2H, m, phth), 8.07 (1 H, d, J=8.3Hz, py), 8.31 (1H, d, J=3.4Hz, py), 8.38 (1H, brs) and 8.62 (1 H, d, J=2.2 Hz).

$^{13}$C nmr (CDCl$_3$); 21.5, 22.7, 24.6, 25.9, 32.3, 36.7, 37.5, 40.4, 41.5, 52.3, 54.7, 123.1, 123.6, 126.1, 126.6, 127.3, 128.4, 129.1, 131.2, 134.0, 136.3, 140.9, 144.6, 169.6.

The following compounds were prepared using synthetic procedures analogous to those described for the above examples 5 and 6.

EXAMPLE 7

Thioacetic acid 1S-{1S-[2,2-dimethyl-1S-(pyridin-2-ylcarbamoyl)-propylcarbamoyl]-3-methyl-butylcarbamoyl}-4-(1,3-dioxo-1,3-dihydro-isoindol-2-yl)-butyl ester

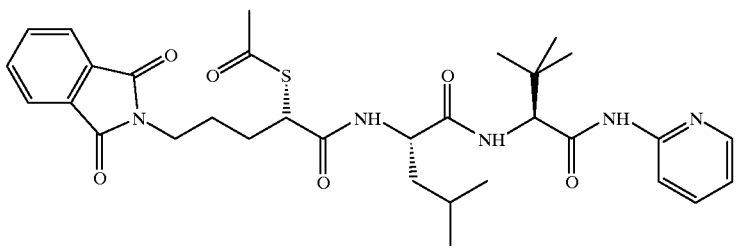

¹H nmr (CDCl₃); 0.75 (3H, d, J=6.4 Hz, Leu), 0.81 (3H, d, J 6.2 Hz, Leu), 1.03 (9H, s, tBu), 1.44–2.05 (7H, m), 2.30 (3H, s, MeCO), 3.58 (2H, t, J=6.4 Hz, CH₂N), 3.70 (1H, brt), 3.72 (1H, brs), 4.07 (1H, m), 4.58 (1H, m), 5.27 (1H, m), 6.85 (1 H, m), 7.10 (1H, dd, J=7.3 and 12.3 Hz, py), 7.69 (2H, m, phthalimide), 7.71–7.87 (3H, m, phth & py), 8.35 (1 H, d, J=8.5 Hz, py) and 8.48 (1 H, d, J=4.4 Hz, py).

¹³C nmr (CDCl₃); 21.2, 23.1, 24.7, 26.1, 26.5, 28.0, 30.2, 35.8, 37.2, 46.8, 52.1, 60.6, 114.5, 120.0, 123.1, 132.0, 133.6, 139.0, 147.5, 151.3, 168.0, 170.5, 171.0, 173.3, 194.7.

EXAMPLE 8

5-(1,3-Dioxo-1,3-dihydro-isoindol-2-yl)-2S-mercaptopentanoic acid {S-[2,2-dimethyl-1S-(pyridin-2-ylcarbamoyl)-propylcarbamoyl]-3-methyl-butyl}-amide ¹H nmr (CDCl₃); 0.80 (3H, d, J=5.6 Hz, Leu), 0.88 (3H, d, J=5.8 Hz, Leu), 1.25–1.96 (7H, m), 2.40 (3H, s, COMe), 3.23 (1 H, dd, J=9.3 & 14.2 Hz, CHₐHᵦPh), 3.46 (1H, dd, J=5.2 & 14.2 Hz, CHₐCHᵦPh), 3.66 (2H, brt, CH₂N), 4.10 (2H, m), 4.90 (1 H, ddd, J=3.2, 5.2 & 8.5 Hz), 6.68 (1 H, d, J=4.3 Hz, NH), 6.75 (1 H, d, J=8.5 Hz, NH), 7.27 (5H, m, Ph), 7.58 (2H, brd, J=6.3 Hz), 7.72 (2H, m, phth), 7.79 (2H, m, phth), 8.41 (2H, d, J=6.3 Hz, py) & 8.68 (1H, brs, NH).

¹³C nmr (CDCl₃-DCI); 21.3, 22.6 24.5, 25.7, 27.0, 30.3, 36.4, 36.7, 39.7, 45.3, 53.7, 55.3, 115.0, 123.2, 126.9, 128.5, 129.1, 131.6, 134.1, 136.1, 141.0, 153.2, 168.4, 172.0, 172.3, 172.7 and 196.5.

$\upsilon_{max}$ cm⁻¹ 1771, 1712 (vs), 1651, 1594 and 1519.

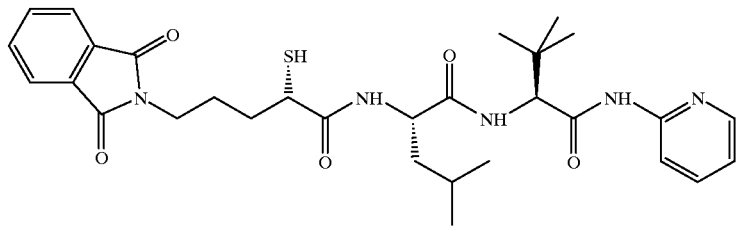

¹H nmr (CDCl₃); 0.83 (3H, d, J=6.5 Hz, Leu), 0.92 (3H, d, J=6.6 Hz, Leu), 1.01 (9H, s, tBu), 1.35–2.05 (7H, m), 3.26 (1H, m), 3.61 (2H, t, J=6.6 Hz, CH₂N), 3.65 (1H, m), 4.67 (1H ,m), 5.14 (1H, m), 6.83 (1 H, d, J=8.6Hz), 7.15 (1H, brdd, J=5.7, 6.5 Hz, py), 7.71 (2H, dd, J=3.0, 5.4 Hz, phth), 7.82 (3H, m, phth & py), 8.32 (1 H, brd, py), 8.40 (1H, d, J=9.5 Hz, py) and 8.51 (1H, brm).

EXAMPLE 9

Thioacetic acid 1S-{1S-[2-phenyl-1S-(pyridin-4-ylcarbamoyl)-ethylcarbamoyl]-3-methyl-butylcarbamoyl}-4-(1,3-dioxo-1,3-dihydro-isoindol-2-yl)-butyl ester

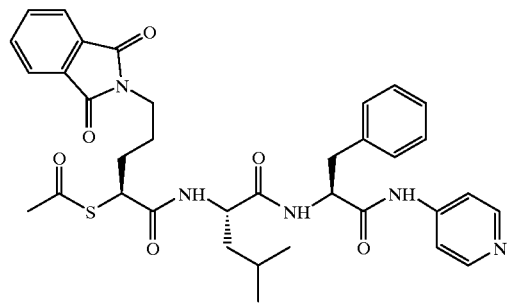

EXAMPLE 10

5-(1,3-Dioxo-1,3-dihydro-isoindol-2-yl)-2S-mercaptopentanoic acid {3-methyl-1S-[2-phenyl-1S-(pyridin-4-ylcarbamoyl)-ethylcarbamoyl]-butyl}-amide

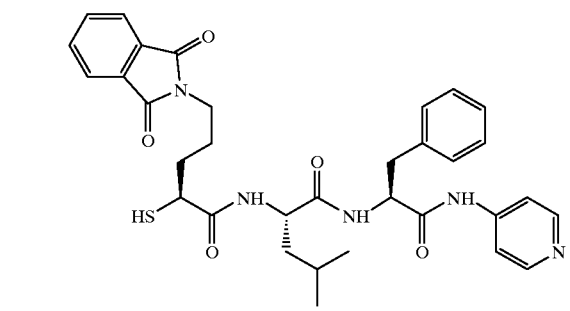

¹H nmr (CDCl₃); 0.85 (3H, d, J=5.8 Hz, Leu), 0.90 (3H, d, J=5.7 Hz, Leu), 1.43–1.92 (7H, m), 3.12 (1H, m), 3.22 (2H, brd, J=6.5 Hz, CH₂Ph), 3.36 (1H, m), 3.68 (2H, m, CH₂N), 4.24 (1 H, m), 4.83 (1H, m), 6.81 (2H, m, NH), 7.21 (5H, m), 7.52 (2H, m, py), 7.72 (2H, m, phth), 7.82 (2H, m, phth), 8.41 (2H, m, py) and 8.68 (1 H, brs, NH).

¹³C nmr (CDCl₃); 21.5, 22.7, 24.7, 25. 7, 32.1. 36.5, 36.7, 40.0, 41 6, 53.4, 54.7, 113.9, 123.2, 127.1, 128.6, 129.0, 131.7, 134.0, 136.2, 146.7, 168.4, 170.2, 171.9, 173.0.

$\upsilon_{max}$ cm⁻¹ 1770, 1712 (vs), 1651 and 1593.

EXAMPLE 11

Thioacetic acid 1S-{1S-[2,2-dimethyl-1S-(pyridin-2-ylcarbamoyl)-propylcarbamoyl]-3-methyl-butylcarbamoyl}-5-(1,3-dioxo-1,3-dihydro-isoindol-2-yl)-pentyl ester

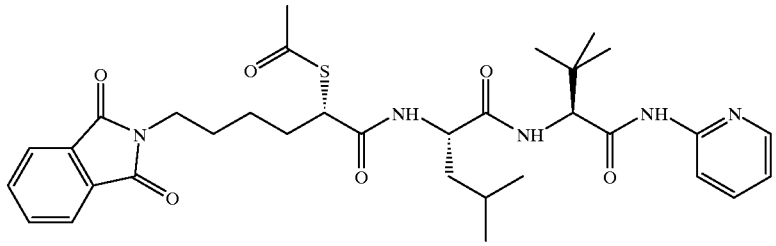

$^1$H nmr (CDCl$_3$); 0.75 (3H, d, J=5.4 Hz, Leu), 0.80 (3H, d, J=5.4 Hz),), 1.05 (9H, s, tBu), 1.32–1.81 (9H, m), 2.30 (3H, s, COMe), 3.52 (2H, t, J=7.4 Hz, CH$_2$N), 4.02 (1H, t, J=7.4 Hz, CH$_2$S), 4.62 (1 H, m, alpha-Leu), 5.34 (1 H, d, J=9.7 Hz, CHtBu), 6.93 (1H, m, NH), 7.08 (1 H, dd, J=5.1, 6.5Hz), 7.69 (3H, m, phth & py), 7.76 (2H, m, phth), 8.31 (1H, d, J=8.4 Hz, py), 8.47 (1 H, brd, J=4.3 Hz, py) and 8.71 (1 H, brs, NH).

$^{13}$C nmr (CDCl$_3$); 21.1, 23.0, 23.9, 24.0, 24.6, 26.3, 27.8, 30.1, 30.9, 35.6, 37.3, 40.8, 47.0, 60.6, 114.3, 119.9, 123.0, 131.9, 133.8, 138.7, 147.5, 151.0, 168.0, 170.2, 171.3, 173.0 and 195.2.

$\upsilon_{max}$ cm$^{-1}$ (KBr) 1772, 1714 (vs), 1651 (s), 1537 and 1435.

EXAMPLE 12

6-(1,3-Dioxo-1,3-dihydro-isoindol-2-yl)-2S-mercaptohexanoic acid {1S-[2,2-dimethyl-1S-(pyridin-2-ylcarbamoyl)-propylcarbamoyl]-3-methyl-butyl}-amide

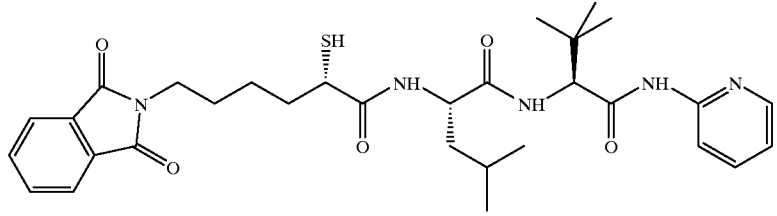

$^1$H nmr (CDCl$_3$); 0.80 (3H, d, J=6.5 Hz, Leu), 0.91 (3H, d, J=6.5 Hz, Leu), 1.05 (9H, s, tBu), 1.26–2.02 (9H, m), 3.18 (1H, m), 3.56 (2H, m, CH$_2$N), 3.66 (1H, m), 4.73 (1H, m, alpha-Leu), 5.32 (1H, d, J=7.8 Hz, CHtBu), 6.79 (1H, brm, NH), 7.11 (1H, dd, J=7.1, 7.3 Hz, py), 7.68–7.74 (3H, m, py & phth), 7.78–7.83 (2H, m, phth), 8.34 (2H, d, J=4.9 Hz, py) and 8.38 (1 H, brs, NH).

$^{13}$C nmr (CDCl$_3$); 21.3, 23.0, 24.4, 24.6, 26.4, 27.8, 35.6 (x2), 35.65, 37.3, 41.4, 42.4, 51.4, 114.3, 120.0, 123.0, 131.9, 133.7, 139.0, 146.7, 168.3, 170.2, 172.7 and 173.2.

$\upsilon_{max}$ cm$^{-1}$ (KBr) 1773, 1719 (vs), 1649 (s), 1531 and 1434

EXAMPLE 13

5-(1,3-Dioxo-1,3-dihydro-isoindol-2-yl)-2S-mercaptopentanoic acid {1S-[2,2-dimethyl-1S-(pyridin-2-ylcarbamoyl)-propylcarbamoyl]-3-methylthio-propyl}-amide

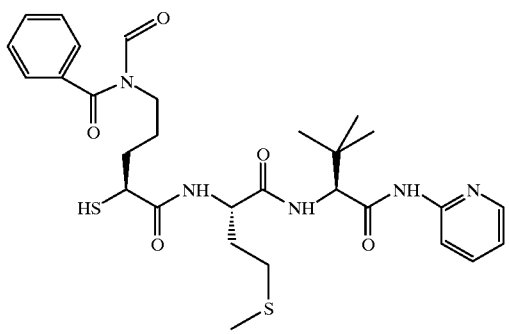

$^1$H nmr (CDCl$_3$); 1.02 (9H, s, tBu), 1.53–1.90 (4H, m), 2.02 (3H, s, MeS), 2.12 (1 H, m, CH$_a$H$_b$CH$_2$S), 2.29 (1 H, m, CH$_a$H$_b$CH$_2$S), 2.57 (2H, t, J=7.2 Hz, CH$_2$S), 3.31 (1 H, m), 3.62 (2H, t, J=6.4 Hz, CH$_2$N), 4.92 (1 H, m), 5.18 (1 H, d, J=9.2 Hz, CHtBu), 7.09 (1 H, dd, J=6.8, 6.4 Hz), 7.16 (1 H, d, J=6.1 Hz), 7.70 (3H, m, phth & py), 7.81 (3H, m, phth & py), 8.33 (1 H, dd, J=2.5, 4.8 Hz, py), 8.35 (1 H, S, NH), and 8.76 (1 H, d, J=3.7Hz, NH).

$^{13}$H nmr (CDCl$_3$-DCI); 15.0, 26.1, 26.3, 30.0, 30.5, 32.5, 34.4, 37.1, 41.4, 52.7, 62.6, 117.2, 120.4, 123.1, 134.0, 137.1, 147.0, 168.5.

EXAMPLE 14

Thioacetic acid 1S-{1S-[2,2-dimethyl-1S-(pyrdin-2-ylcarbamoyl)-propylcarbamoyl]-3-methylthio-propylcarbamoyl}-4-(1,3-dioxo-1,3-dihydro-isoindol-2-yl)-butyl ester

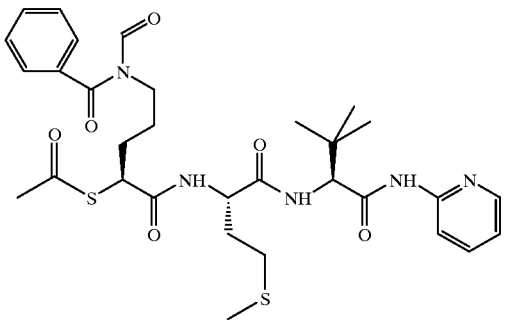

¹H nmr (CDCl₃); 1.04 (9H, s, tBu), 1.66–1.92 (4H, m), 1.99 (3H, s, MeS), 2.02 (1 H, m), 2.32 (3H, s, MeCO), 2.37 (1 H. m), 2.52 (2H, t, J=7.2 Hz), 3.58 (1 H, brt, J=6.3 Hz), 3.69 (I H, m), 3.72 (1 H, s, NH), 4.08 (1 H, m), 4.77 (1 H, dd, J=7.7 and 15.4 Hz, Met α-H), 5.19 (1H, d, J=9.6Hz, α-H), 7.02 (1H, brd, J=8.7Hz), 7.07 (1H, dd, J=5.0 & 6.6 Hz, py), 7.67–7.78 (3H, m, phth & py), 7.80–7.87 (2H, m, phth), 8.33 (1 H, d, J=8.3 Hz, py), 8.48 (1H, brd, J=3.8Hz, py) and 8.64 (1H, brs).

¹³C nmr (CDCl₃); 15.1, 26.0, 26.4, 26.6, 30.2, 30.3, 31.8, 35.5, 37.1, 46.8, 52.2, 60.7, 114.3, 120.0, 123.1, 131.9, 133.8, 138.8, 147.7, 151.2, 168.0, 169.9, 170.9, 171.9 and 194.9.

EXAMPLE 15

5-(1,3-Dioxo-1,3-dihydro-isoindol-2-yl)-2S-mercaptopentanoic acid {1 S-[2,2-dimethyl-1S-(thiazol-2-ylcarbamoyl)-propylcarbamoyl]-3-methyl-butyl}-amide

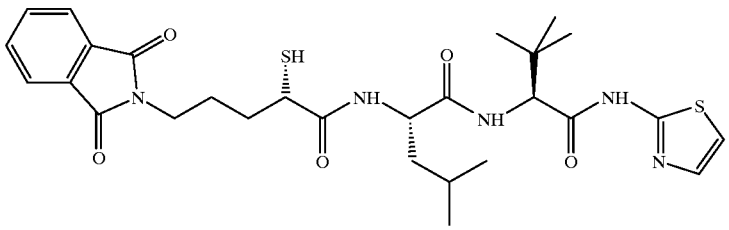

¹H nmr (MeOD); 0.77 (3H, d, J=1.1 Hz, Leu), 0.79 (3H, d, J=1.2 Hz, Leu), 0.87 9H, s, tBu), 1.29–1.69 (7H, m), 3.28 (1H, m, CHS), 3.53 (2H, m CH₂N), 4.45 (1H, m), 4.61 (1 H, s, CHtBu), 7.00 (1 H, d, J=3.8 Hz, NCH=), 7.35 (1 H, d, J=3.8 Hz, SCH=), 7.70 (4H, m, phth).

¹³C nmr (MeOD); 24.3, 25.9, 26.3, 28.3, 29.4, 30.1, 37.0, 38.5, 40.5, 44.1, 44.6, 55.7, 64.1, 117.2, 126.6, 135.8, 137.7, 140.8, 172.1, 172.9, 178.0 and 182.3.

EXAMPLE 16

Thioacetic acid 1S-{1S-[2,2-dimethyl-1S-(thiazol-2-ylcarbamoyl)-propylcarbamoyl]-3-methyl-butylcarbamoyl}-4-(1,3-dioxo-1,3-dihydro-isoindol-2-yl)-butyl ester

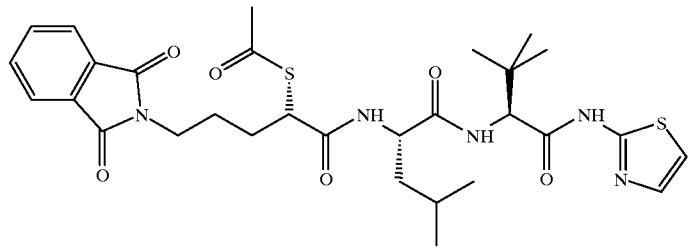

¹H nmr (CDCl₃); 0.77 (6H, m, (CH₃)₂), 1.01 (9H, s, tBu), 1.48 (1 H, m), 1.52–1.82 (5H, brm), 2.02 (1 H, m), 2.30 (3H, s, COMe), 3.59 (2H, m, CH₂N), 4.28 (1 H, m), 4.58 (1 H, m), 5.28 (1 H, m), 7.00 (1 H, d, J=3.7 Hz, NH), 7.70 (4H, m, phth, SCH=& NH), 7.83 (3H, m, phth & NCH=) and 8.83 (1H, brs, NH).

EXAMPLE 17

5-(1,3-Dioxo-1,3-dihydro-isoindol-2-yl)-2S-mercaptopentanoic acid {1 S-[2,2-dimethyl-1S-(pyridin-4-ylcarbamoyl)-propylcarbamoyl]-3-methyl-butyl}-amide

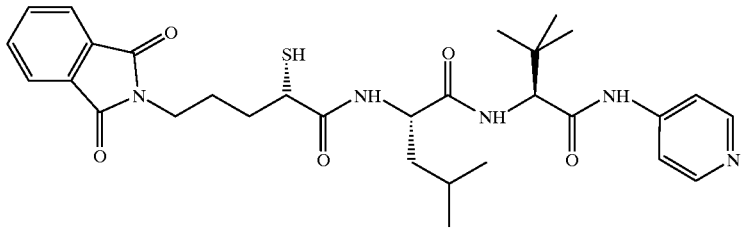

$^1$H nmr (MeOD); 0.79 (3H, d, J=6.4 Hz, Leu), 0.83 (3H, d, J=6.5 Hz, Leu), 0.86 (9H, s, tBu), 1.48–1.83 (7H, m), 3.29 (1H, m), 3.58 (2H, m, CH$_2$N), 4.31 (1 H, s, CHtBu), 4.37 (1 H, m), 7.55 (2H, m, py), 7.65–7.73 (4H, m, phth) and 8.27 (2H, d, J=4.9 Hz, py).

$^{13}$C nmr (MeOD); 21.9, 23.5, 25.9, 27.0, 27.7, 34.6, 36.0, 38.2, 41.5, 42.2, 53.2, 62.6, 115.2, 124.1, 133.4, 135.3, 147.6, 150.7, 169.8, 172.0, 174.4 and 175.7.

EXAMPLE 18

Thioacetic acid 1S-{1S-[2,2-dimethyl-1S-(pyridin-4-ylcarbamoyl)-propylcarbamoyl]-3-methyl-butylcarbamoyl}-4-(1,3-dioxo-1,3-dihydro-isoindol-2-yl)-butyl ester

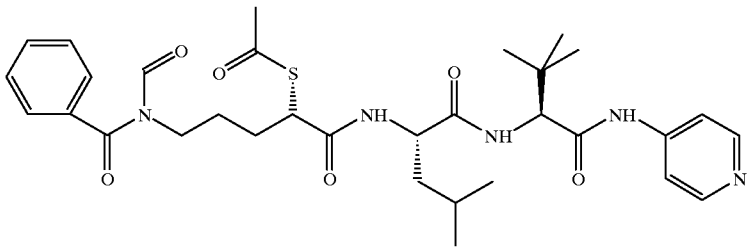

$^1$H nmr (CDCl$_3$); 0.86 (3H, d, J=6.1 Hz, Leu), 0.91 (3H, d, J=6.2 Hz, Leu), 1.01 (9H, s, tBu), 1.63–1.79 (7H, brm), 2.37 (3H, s, SCOMe), 3.70 (3H, m, CH$_2$N &CHS), 4.16 (1H, m), 4.51 (1H, m), 7.13 (1H, brdd, NH), 7.57 (1H, brd, J=5.4Hz, NH), 7.64–7.73 (4H, m, phth & py), 7.83 (2H, m, phth), 8.43 (2H, brd, J=4.6 Hz, py), 9.3 (1H, brs, NH).

EXAMPLE 19

Thioacetic acid 1S-{1S-[2,2-dimethyl-1S-(pyridin-2-ylcarbamoyl)-propylcarbamoyl]-3-methylthio-propylcarbamoyl}-5-(1,3-dioxo-1,3-dihydro-isoindol-2-yl}pentyl ester

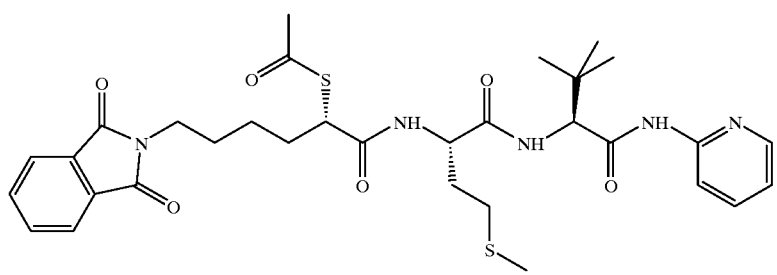

¹H nmr (CDCl₃); 1.06 (9H, s, tBu), 1.27–1.54 (2H, m), 1.7–1.86 (4H, m), 1.95–2.03 (2H, m), 1.99 (3H, s, COMe), 2.35 (3H, s, SMe), 2.53 (2H, t, J=7.0 Hz, CH₂S), 3.54 (2H, t, J=7.2 Hz, CH₂N), 3.65 (1 H, m), 4.02 (1 H, brt, J=7.3 Hz), 4.81 (1 H, dd, J=7.9, 15.5 Hz), 5.23 (1H, d, J=9.7 Hz), 7.03 (1H, brd, J=12.2 Hz), 7.08 (1H, dd, J=5.9, 7.2 Hz, py), 7.52–7.70 (3H, m, phth & py), 7.72–7.83 (2H, m, phth), 8.29 (1H, d, J=8.5 Hz, py), 8.48 (1 H, d, J=4.2 Hz, py) and 8.74 (1 H, brm, NH).

¹³C nmr (CDCl₃); 15.1, 24.0, 26.4, 27.8, 29.9, 30.2, 30.8, 31.9, 35.4, 37.2, 47.3, 52.1, 60.7, 114.2, 120.0, 123.0, 132.0, 133.7, 138.8, 147.6, 151.2, 168.0, 170.0, 171.2, 172.0, 195.2.

EXAMPLE 20
6-(1,3-Dioxo-1,3-dihydro-isoindol-2-yl)-2S-mercaptohexanoic acid {1 S-[2,2-dimethyl-1S-(pyridin-4-ylcarbamoyl)-propylcarbamoyl]-3-methyl-butyl}-amide

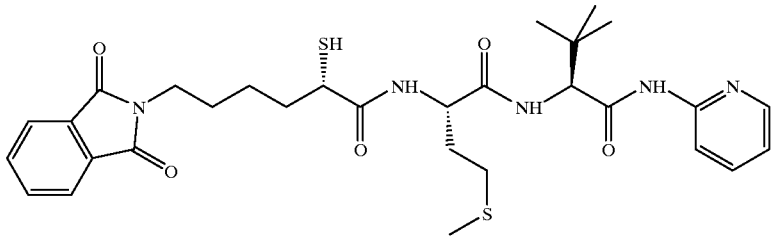

¹H nmr (CDCl₃); 1.05 (9H, s, tBu), 1.31–1.9 (6H, m), 1.99–2.11 (2H, m), 2.03 (3H, s, SMe), 2.58 (2H, t, J=7.1 Hz, CH₂S), 3.19 (1H, dd, J=7.2, 17.2 Hz, CHS), 3.60 (2H, t, J=7.4 Hz, CH₂N), 4.83 (~1 H, m, NH), 4.95 (1H, dd, J=8.1 Hz, Met-α), 5.25 (1H, d, J=9.3 Hz, CHtBu), 7.08 (1 H, dd, J=6.3, 6.4 Hz, py), 7.21 (1 H, brd, J=10.9 Hz, NH), 7.68–7.73 (3H, m, py and phth), 7.76–7.87 (2H, m, phth), 8.31 (1 H, d, J=8.8 Hz, py), 8.36 (1 H, brs, py), 8.81 (1H, brs, NH), 10.53 (1H, brs).

¹³C nmr (CDCl₃); 15.2, 24.4, 26.5, 27.8, 30.3, 32.4, 35.5, 35.7, 37.3, 42.5, 51.6, 60.7, 114.4, 120.0, 123.0, 132.0, 133.7, 138.9, 147.1, 151.2, 168.1, 170.0, 172.1, 173.0.

EXAMPLE 21
Thioacetic acid 1S-{2-(biphenyl-4-ylmethylthio)-1S-[2,2-dimethyl-1S-(pyridin-4-ylcarbamoyl)-propylcarbamoyl]-ethylcarbamoyl}-4-(1,3-dioxo-1,3-dihydro-isoindol-2-yl}butyl ester

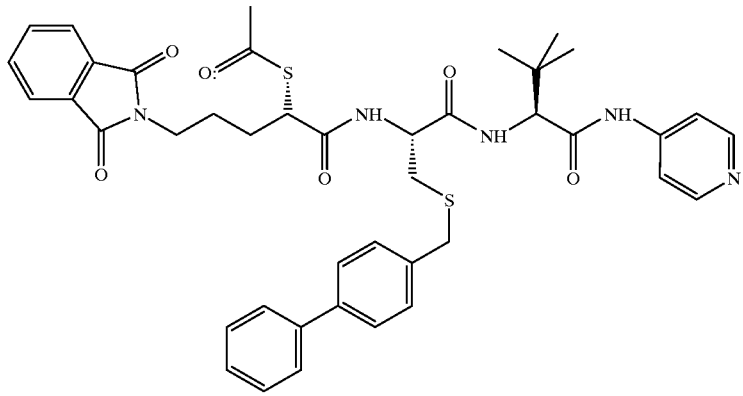

¹H nmr (CDCl₃); 1.04 (9H, s, tBu), 1.71–2.04 (4H, m), 2.37 (3H, s, COCH₃), 2.90 (2H, m, J=6.4 Hz, CH₂S), 3.70 (2H, brt, J=5.9 Hz, CH₂N), 3.78 (2H, s, SCH₂Ar), 4.17 (1 H, dd, J=6.0, 7.2 Hz), 4.37 (1 H, d, J=8.3 Hz, CHtBu), 4.50 (1 H, dd, J=6.3, 12.5 Hz), 7.07 (1 H, d, J=8.3 Hz, NH), 7.22 (1 H, d, J=6.4 Hz, NH), 7.30–7.46 (5H, m, Ar & py), 7.51–7.57 (4H, m, Ar & phth), 7.71 (4 H, m, phth & Ar), 7.82 (2H, m, phth), 8.46 (2H, brd, J=6.3 Hz, py) and 8.98 (1 H, brs, NH).

EXAMPLE 22

5-(1,3-Dioxo-1,3-dihydro-isoindol-2-yl)-2S-mercaptopentanoic acid {2-(biphenyl-4-ylmethylthio)-1S-[2,2-dimethyl-1S-(pyridin-4-ylcarbamoyl)-propylcarbamoyl]-ethyl}amide

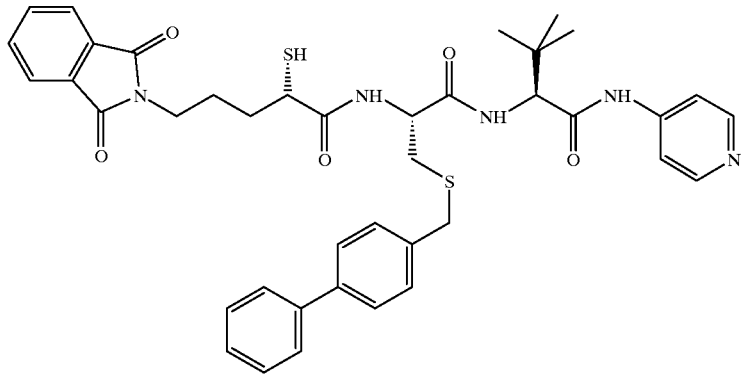

$^1$H nmr (CD$_3$OD); 0.97 (9 H, s, tBu), 1.61–1.89 (4 H, m), 1.97 (1 H, brdd), 2.78 (2 H, d, J=7.4 Hz, CHCH$_2$S), 3.27 (2 H, brt, J=6.2 hz, CH$_2$N), 3.35 (1 H, brt, CHS), 3.71 (2 H, s, ArCH$_2$S), 4.33 (1 H, s, CHtBu), 4.46 (1 H, t, J=6.5 Hz, CHCH$_2$S), 7.05–7.45 (13 H, Ar & phth), 7.67 (2 H, dd, J=1.5, 4.9 Hz, py), 8.25 (2 H, dd, J=1.5, 4.9 Hz, py). 3 exchangeable NH protons.

What is claimed is:

1. A compound of formula (I)

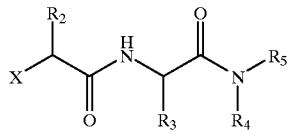

wherein

X is a group of formula (II)

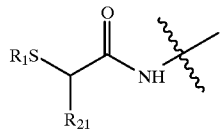

$R_2$ is a group —(Alk)$_m$—(Q)$_n$—Z wherein
m and n are independently 0 or 1,
Alk represents (C$_1$–C$_6$)alkyl,
Q represents —O—, —S—, —SO— or SO$_2$—, and
Z represents hydrogen, or an optionally substituted (C$_1$–C$_6$)alkyl, (C$_3$–C$_7$)cycloalkyl, or phenyl group;
$R_1$ is hydrogen or a group $R_{20}$C(O)— where $R_{20}$ is a (C$_1$–C$_6$)alkyl;
$R_{21}$ is hydrogen or a phthalimido(C$_1$–C$_4$)alkyl- or optionally methyl-substituted 2,5-dioxo-1-imidazolidinyl (C$_1$–C$_6$)alkyl group;
$R_3$ is the side chain of a natural α-amino acid in which any functional groups may be protected, or a group selected from 4-chlorophenylmethyl, 2-thienylmethyl, iso-butyl or 1-benzylthio-1-methylethyl, benzyl, t-butyl or 1-mercapto-1-methylethyl,
$R_4$ is a phenyl or pyridyl, thiazolyl, or quinolyl ring wherein any ring nitrogen atom may be oxidized as an N-oxide, and wherein any of the rings may be optionally substituted by:

(a) one or more substituents independently selected from hydroxyl, halogen, —CN, —CO$_2$(C$_1$–C$_6$)alkyl, —(C$_1$–C$_6$)alkyl-CO$_2$(C$_1$–C$_6$)alkyl, —CONH$_2$, —CONH(C$_1$–C$_6$)alkyl, —CON(C$_1$–C$_6$)alkyl)$_2$, —CHO, —CH$_2$OH, —(C$_1$–C$_4$)perfluoroalkyl, —O(C$_1$–C$_6$)alkyl, —S(C$_1$–C$_6$)alkyl, —SO(C$_1$–C$_6$)alkyl, —SO$_2$(C$_1$–C$_6$)alkyl, —NO$_2$, NH$_2$ —NH(C$_1$–C$_6$)alkyl, —N((C$_1$–C$_6$)alkyl)$_2$, and —NHCO(C$_1$–C$_6$)alkyl, or (b) a group selected from (C$_1$–C$_6$)alkyl, (C$_2$–C$_6$)alkenyl, (C$_2$–C$_6$)alkynyl, (C$_3$–C$_8$)cycloalkyl, (C$_4$–C$_8$)cycloalkenyl, phenyl, benzyl, heteroaryl or heteroarylmethyl any of which groups may be optionally substituted with one or more substituents selected from halogen, hydroxyl, amino, carboxyl, (C$_1$–C$_4$)perfluoroalkyl, (C$_1$–C$_6$)alkyl, —O(C$_1$–C$_6$) alkyl or —S(C$_1$–C$_6$)alkyl;
$R_5$ is hydrogen or a (C$_1$–C$_6$)alkyl group;
or a salt, hydrate or solvate thereof.

2. A compound as claimed in claim 1 wherein the stereochemistry is as follows;
C atom carrying the $R_{21}$ group —S,
C atom carrying the $R_2$ group —S,
C atom carrying the $R_3$ group —S.

3. A compound as claimed in claim 1 wherein $R_{21}$ is phthalimidopropyl, phthalimidobutyl, phthalimidoethyl, phthalimidomethyl, 3,4,4-trimethyl-2,5-dioxo-1-imidazoidinylpropyl, 3,4,4-trimethyl-2,5-dioxo-1-imidazolidinyethyl, or 3,4,4-trimethyl-2,5-dioxo-1-imidazolidinylmethyl.

4. A compound as claimed in claim 1 wherein $R_2$ is n-pentyl, n-hexyl, n-heptyl, n-nonyl, n-decyl, 2-ethylthioethyl, ethylthiomethyl, propylthiomethyl, butylthiomethyl, phenylpropyl, 4-chlorophenylpropyl, 4-methylphenylpropyl, 4-methoxyphenylpropyl, 2-benzylthioethyl, benzylthiomethyl, or phenoxybutyl.

5. A compound as claimed in claim 1 wherein $R_2$ is iso-butyl, 2-methylthioethyl, n-octyl, benzyloxypropyl, phenoxybutyl, 4-phenyl-phenylpropyl, or 4-phenylbenzylthiomethyl.

6. A compound as claimed in claim 1 wherein $R_4$ is phenyl, thiazol-2-yl, 4,5-dimethylthiazol-2-yl, or quinolin-3-yl.

7. A compound as claimed in claim 1 wherein $R_4$ is 3-methoxyphenyl, pyridin-2-yl, pyridin-3-yl, pyridin-4-yl, thiazol-2-yl, 4-ethoxycarbonylmethylthiazol-2-yl, 5-methyl-1,3,4-thiadiazol-2-yl or 4-tert-butylthiazol-2-yl.

8. A compound as claimed in claim 1 wherein $R_5$ is hydrogen, methyl or ethyl.

9. A compound as claimed in claim 1 wherein $R_{21}$ is n-propyl, phthalimidopropyl, phthalimidobutyl, phthalimidoethyl, phthalimidomethyl, 3,4,4-trimethyl-2,5-dioxo-1-imidazolidinylpropyl, 3,4,4-trimethyl-2,5-dioxo-1-imidazolidinyethyl, or 3,4,4-trimethyl-2,5-dioxo-1-imidazolidinylmethyl; $R_2$ is iso-butyl, 2-methylthioethyl, n-octyl, benzyloxypropyl, phenoxybutyl, 4-phenylphenylpropyl, or 4-phenylbenzylthiomethyl; $R_4$ is 3-methoxyphenyl, pyridin-2-yl, pyridin-3-yl, pyridin-4-yl, thiazol-2-yl, 4-ethoxycarbonylmethylthiazol-2-yl, 5-methyl-1,3,4-thiadiazol-2-yl or 4-tert-butylthiazol-2-yl; and $R_5$ is hydrogen, methyl or ethyl.

10. A pharmaceutical composition comprising a compound as claimed in claim 1 together with a pharmaceutically acceptable carrier.

* * * * *

UNITED STATES PATENT AND TRADEMARK OFFICE
CERTIFICATE OF CORRECTION

PATENT NO.: 6,103,739

DATED: August 15, 2000

INVENTOR: Christopher D. FLOYD, *et al.*

It is certified that an error appears in the above-identified patent and that said Letters Patent is hereby corrected as shown below:

In Claim 1, column 29, line 60:

"$(C_1-C_6)$" has been replaced with —$(C_1-C_4)$—

Signed and Sealed this

Fifteenth Day of May, 2001

*Attest:*

NICHOLAS P. GODICI

*Attesting Officer*    Acting Director of the United States Patent and Trademark Office